United States Patent [19]
Weidmann et al.

[11] Patent Number: 6,020,350
[45] Date of Patent: Feb. 1, 2000

[54] 3-HYDROXYPYRIDINE-2-CARBOXAMIDOESTERS, THEIR PREPARATION AND THEIR USE AS PHARMACEUTICALS

[75] Inventors: Klaus Weidmann, Kronberg; Karl-Heinz Baringhaus, Wölfersheim; Georg Tschank, Essenheim; Martin Bickel, Bad Homburg, all of Germany

[73] Assignee: Hoechst Aktiengesellschaft, Frankfurt am Main, Germany

[21] Appl. No.: 08/985,266

[22] Filed: Dec. 4, 1997

[30] Foreign Application Priority Data

Dec. 4, 1996 [DE] Germany ............ 196 50 215

[51] Int. Cl.$^7$ .................. C07D 213/65; C07D 213/89; A61K 31/44
[52] U.S. Cl. .................. 514/346; 546/296; 546/298
[58] Field of Search .................. 546/296, 298; 514/346

[56] References Cited

U.S. PATENT DOCUMENTS

| | | | |
|---|---|---|---|
| 5,204,338 | 4/1993 | Baader et al. ............ | 514/183 |
| 5,620,995 | 4/1997 | Weidmann et al. ............ | 514/350 |
| 5,719,164 | 2/1998 | Weidmann et al. ............ | 514/312 |

FOREIGN PATENT DOCUMENTS

| | | |
|---|---|---|
| 0 457 163 A1 | 11/1991 | European Pat. Off. . |
| 0 661 269 A1 | 7/1995 | European Pat. Off. . |
| 0 765 871 | 4/1997 | European Pat. Off. . |

OTHER PUBLICATIONS

C. Jane Cunliffe et al., "Novel Inhibitors of Prolyl 4–Hydroxylase. 3. Inhibition by the Substrate Analogue N–Oxaloglycine and Its Derivatives", J. Med. Chem., 35, 2652–2658, (1992).

John T. Sheehan, "3–Hydroxypicolinic Acid and Some of Its Derivatives", J. Organic Chemistry, vol. 31, No. 3, 636–638, (1996).

T. J. Franklin, et al., "Approaches to the Design of Anti–Fibrotic Drugs", Biochem. Soc. Trans. vol. 19, Jul. 25, 1991, pp. 812–815.

*Primary Examiner*—Alan L. Rotman
*Attorney, Agent, or Firm*—Finnegan, Henderson, Farabow, Garrett & Dunner, L.L.P.

[57] ABSTRACT

There are described 3-hydrixypyridine-2-carboxamidoesters of the formula

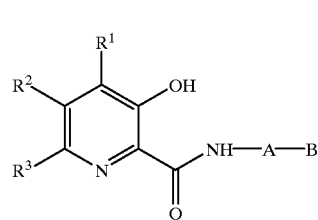

(I)

their preparation, their use for the inhibition of collagen biosynthesis and their use as pharmaceuticals for the treatment of fibrotic disorders.

30 Claims, No Drawings

3-HYDROXYPYRIDINE-2-CARBOXAMIDOESTERS, THEIR PREPARATION AND THEIR USE AS PHARMACEUTICALS

BACKGROUND OF THE INVENTION

The invention relates to 3-hydroxypyridine-2-carboxamidoesters, their preparation and their use for the inhibition of collagen biosynthesis and their use as pharmaceuticals for the treatment of fibrotic disorders.

Compounds which inhibit the enzymes prolyl and lysyl hydroxylase cause a very selective inhibition of collagen biosynthesis by affecting the collagen-specific hydroxylation reactions. In the course thereof, protein-bound proline or lysine is hydroxylated by the enzymes prolyl or lysyl hydroxylase. If this reaction is suppressed by inhibitors, a nonfunctional, underhydroxylated collagen molecule results, which can be released into the extracellular space only in a small amount by the cells. The underhydroxylated collagen additionally cannot be incorporated into the collagen matrix and is very easily proteolytically degraded. As a result of these effects, the amount of extracellularly deposited collagen is decreased overall.

Inhibitors of prolyl hydroxylase are therefore suitable substances in the therapy of disorders in which the deposition of collagens decisively contributes to the clinical picture. These include, inter alia, fibroses of the lung, liver and skin (scleroderma and scars after burns, injuries and surgical interventions) and also atherosclerosis.

It is known that the enzyme prolyl hydroxylase is effectively inhibited by pyridine-2,4- and -2,5-dicarboxylic acid (K. Majamaa et al., *Eur. J. Biochem.* (1984), 138: 239–245). In cell culture, however, these compounds are only active as inhibitors in very high concentrations (Tschank, G. et al., *Biochem. J.* (1987), 238: 625–633).

Prodrugs of the pyridine-2,4(5)-dicarboxylates are also known. These are described in the patent applications Ser. Nos. EP-A-O 590 520, DE-A42 38 506, and EP-A-O 562 512. N-Oxalylglycines as inhibitors of prolyl-4-hydroxylase are known from *J. Med. Chem.* (1992), 35: 2652–2658 (Cunliffe et al.) and EP-A-O 457 163. 3-Hydroxypyridine-2-carboxylic acid (glycyl)amides and their prodrugs, and their use, are disclosed in EP-A-O 661 269. Furthermore, 3-hydroxypyridine-2-carboxylic acid ((glycyl) ethyl ester) amide is described in *J. Org. Chem.* (1966), 31: 636–638.

SUMMARY OF THE INVENTION

It was therefore the object to provide compounds which are distinguished by a particularly high in vivo and/or in vitro activity, in particular in their systemic and/or local use.

Surprisingly, it has now been found that 3-hydroxypyridine-2-carboxamidoesters of the formula I are particularly strong active inhibitors of collagen biosynthesis. They are distinguished by a particularly high in vivo and in vitro activity, in particular in their systemic and/or local use against fibrotic disorders. These include, for example, fibroses of the lung, the liver, the kidney, the heart, the eye, and the skin and in atherosclerosis.

The compounds of the formula I lead to a potent inhibition of collagen biosynthesis in the most diverse cells (e.g. normal human dermal fibroblasts, primary fat storing cells from rat liver, rat liver epithelial cells and in organ cultures of calvaria).

They are particularly suitable for local use as inhibitors of collagen biosynthesis, for local use as antifibrotic active compounds and for local use in forms of disease which are caused by an increased binding of connective tissue (collagen). Thus the compounds of the formula I are suitable, for example, for local use for the avoidance/reduction of scars after surgical interventions on the human body and for local use in the postoperative treatment of ophthalmic disorders, e.g., the postoperative treatment of glaucoma and in radiation-induced fibrosis or fibrosis induced by chemotherapy, in particular in the lung.

The compounds according to the invention are ester prodrugs of the corresponding carboxylic acids of the formula I, in which B is a carboxyl group.

The compounds of the formula I are cleaved in the living body (in vivo) and in cell cultures (in vitro) to give compounds of the formula I in which B is a carboxyl group or its salts of said compounds.

After the administration of the compounds of the formula I, they cause the inhibition of collagen biosynthesis to be observed in vivo and in vitro, the compounds of the formula I in which B is a carboxyl group or its salts of said compounds being formed. These compounds inhibit prolyl-4-hydroxylase and therefore lead to an inhibition of collagen biosynthesis.

The compounds according to the invention correspond to the formula I

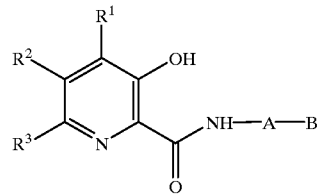

wherein
$R^1$, $R^2$ and $R^3$ are hydrogen,
A is a —$CH_2$— group, in which a hydrogen atom can be replaced by a methyl group, and
B is —$CO_2G$, wherein
G is an organic radical which makes the compounds of the formula I into a prodrug,
or a physiologically active salt of said compounds,
and excluding 3-hydroxypyridine-2-carboxylic acid ((glycyl) ethyl ester)amide.

DESCRIPTION OF THE PREFERRED EMBODIMENTS

Preferred compounds of the formula I wherein
$R^1$, $R^2$, and $R^3$ are hydrogen,
A is a —$CH_2$— group in which a hydrogen atom can be replaced by a methyl group, and
B is —$CO_2G$, wherein
G is the radical of an alcohol GOH,
or a physiologically active salt of said compounds,
and excluding 3-hydroxypyridine-2-carboxylic acid ((glycyl) ethyl ester)amide.
Further preferred compounds of the formula I wherein
$R^1$, $R^2$, and $R^3$ are hydrogen,
A is a —$CH_2$— group, in which a hydrogen atom can be replaced by a methyl group, and
B is —$CO_2G$, wherein
G is a branched or unbranched ($C_1$–$C_{20}$)-alkyl radical, a branched or unbranched ($C_2$–$C_{20}$)-alkenyl radical, a branched or unbranched ($C_2$–$C_{20}$)-alkynyl radical, a branched or unbranched ($C_4$–$C_{20}$)-alkenynyl radical, a ($C_3$–$C_{12}$)-cycloalkyl radical, or a retinyl radical, where the radicals can in each case contain one or more multiple bonds, or is a phenylalkyl radical wherein the above radicals in particular contain one or more substituents selected from hydroxyl, halogen, cyano, trifluoromethyl, carboxyl, ($C_1$–$C_{12}$)-alkyl, ($C_3$–$C_8$)-cycloalkyl, ($C_5$–$C_8$)-cycloalkenyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, phenyl-($C_1$–$C_4$)-alkyloxy, ($C_1$–$C_8$)-hydroxyalkyl, ($C_1$–$C_{12}$)-alkylcarbonyloxy, ($C_3$–$C_8$)-cycloalkylcarbonyloxy, benzoyloxy, and phenyl-($C_1$–$C_4$)-alkylcarbonyloxy, or a physiologically active salt of said compounds, and excluding 3-hydroxypyridine-2-carboxylic acid ((glycyl) ethyl ester)amide.

Further preferred compounds of the formula I are those wherein $R^1$, $R^2$, and $R^3$ are hydrogen, A is a —$CH_2$— group in which a hydrogen atom can be replaced by a methyl group, and B is —$CO_2G$, wherein G is a branched or unbranched aliphatic ($C_1$–$C_{18}$)-alkyl radical, a ($C_3$–$C_8$)-cycloalkyl radical, a ($C_3$–$C_8$)-cycloalkyl-($C_1$–$C_8$)-alkyl radical, a branched or unbranched ($C_2$–$C_{18}$)-alkenyl radical, such as, for example, a geranyl, a farnesyl, a retinyl radical, a branched or unbranched ($C_2$–$C_{18}$)-alkynyl radical, a benzyl, a phenethyl, a phenylpropyl, and phenylbutyl radical, wherein the above radicals contain a substituent selected from hydroxyl, ($C_1$–$C_4$)-alkoxy, ($C_1$–$C_6$)-alkylcarbonyloxy, ($C_3$–$C_8$)-cycloalkylcarbonyloxy, benzoyloxy or phenyl-($C_1$–$C_4$)-alkylcarbonyloxy, or a physiologically active salt of said compounds, and excluding 3-hydroxypyridine-2-carboxylic acid ((glycyl) ethyl ester)amide.

Particularly preferred compounds of the formula I are those wherein $R^1$, $R^2$, and $R^3$ are hydrogen, A is a —$CH_2$— group in which a hydrogen atom can be replaced by a methyl group, and B is —$CO_2G$, wherein G is a branched or unbranched aliphatic ($C_1$–$C_{18}$)-alkyl radical, a ($C_5$–$C_6$)-cycloalkyl radical, a ($C_3$–$C_8$)-cycloalkyl-($C_1$–$C_4$)-alkyl radical, a branched or unbranched ($C_2$–$C_{18}$)-alkenyl radical, a benzyl, a phenethyl, a phenylpropyl, or phenylbutyl radical, or a physiologically active salt of said compounds, and excluding 3-hydroxypyridine-2-carboxylic acid ((glycyl) ethyl ester)amide.

Further particularly preferred compounds of the formula I are those wherein $R^1$, $R^2$, and $R^3$ are hydrogen, A is a —$CH_2$— group, in which a hydrogen atom can be replaced by a methyl group, and B is —$CO_2G$, wherein G is a branched or unbranched ($C_1$–$C_{18}$)-alkyl or ($C_2$–$C_{18}$)-alkenyl radical, or a physiologically active salt of said compounds, and excluding 3-hydroxypyridine-2-carboxylic acid ((glycyl) ethyl ester)amide.

Further particularly preferred compounds of the formula I are those wherein $R^1$, $R^2$, and $R^3$ are hydrogen, A is a —$CH_2$— group, and B is —$CO_2G$, wherein G is a branched or unbranched ($C_1$–$C_{18}$)-alkyl or ($C_2$–$C_{18}$)-alkenyl radical, or a physiologically active salt of said compounds, and excluding 3-hydroxypyridine-2-carboxylic acid ((glycyl) ethyl ester)amide.

In particular, preferred compounds of the formula I are those wherein $R^1$, $R^2$, and $R^3$ are hydrogen, A is a —$CH_2$— group, B is —$CO_2G$, wherein G is a linear ($C_1$–$C_{18}$)-alkyl radical, or a physiologically active salt of said compounds, and excluding 3-hydroxypyridine-2-carboxylic acid ((glycyl) ethyl ester)amide.

Further particularly preferred compounds of the formula I are those wherein $R^1$, $R^2$, and $R^3$ are hydrogen, A is a —$CH_2$— group, B is —$CO_2G$, wherein G is a linear ($C_1$–$C_{16}$)-alkyl radical, or a physiologically active salt of said compounds, and excluding 3-hydroxypyridine-2-carboxylic acid ((glycyl) ethyl ester)amide.

The invention furthermore comprises salts of the compounds of the formula I. Salt formation with acidic reagents can be carried out at the pyridine N atom. Reagents used are, for example, toluenesulfonic acid, methanesulfonic acid, HCl, $H_2SO_4$, $H_3PO_4$ and pharmaceuticals which contain an acidic group.

The invention relates to the compounds of the formula I and to the physiologically tolerable salts thereof for use in the inhibition of collagen biosynthesis.

The invention relates to the compounds of the formula I and to the physiologically tolerable salts thereof for use in the inhibition of prolyl-4-hydroxylase in vivo and in vitro.

The invention further relates to the compounds of the formula I and the physiologically tolerable salts thereof for use in fibrotic disorders of the lung, the liver, the kidney, the heart, the eye and the skin. The compounds can also be used in atherosclerosis. In this connection, systemic and/or local applications are used.

In particular, the invention relates to compounds of the formula I and to the physiologically tolerable salts thereof for local use, in particular as inhibitors of collagen biosynthesis, as antifibrotic active compounds and in forms of disease which are caused by an increased formation of connective tissue (collagen). These include the uses for the avoidance/reduction of scars after surgical interventions on the human body and in the postoperative treatment of eye operations, e.g. in glaucoma operations and in radiation-induced fibrosis or fibrosis induced by chemotherapy, in particular in the lung.

Finally, the invention relates to the compounds of the formula I for use as pharmaceuticals, and to pharmaceutical compositions comprising said compounds. In particular, the invention relates to compounds of the formula I for local use in fibrosis of the skin, the lung and the eye, in particular for the postoperative treatment of glaucoma.

The invention further relates to a process for the preparation of compounds of the formula I. The compounds of the formula I, in which A is a —$CH_2$— group in which a hydrogen can be replaced by a methylene group and B is $CO_2G$, are prepared by i1) reacting pyridine-2-carboxylic acids of the formula II ($R^5$=H) with the amino esters of the formula III or their salts to give the amidoesters of the formula I; or i2) reacting pyridine-2-carboxylic acid esters of the formula II ($R^5$=lower alkyl=($C_1$–$C_5$)-alkyl) under the conditions of aminolysis to give the compounds of the formula I; or ii) esterifying the compounds of the formula IV with an alcohol GOH.

Scheme 1

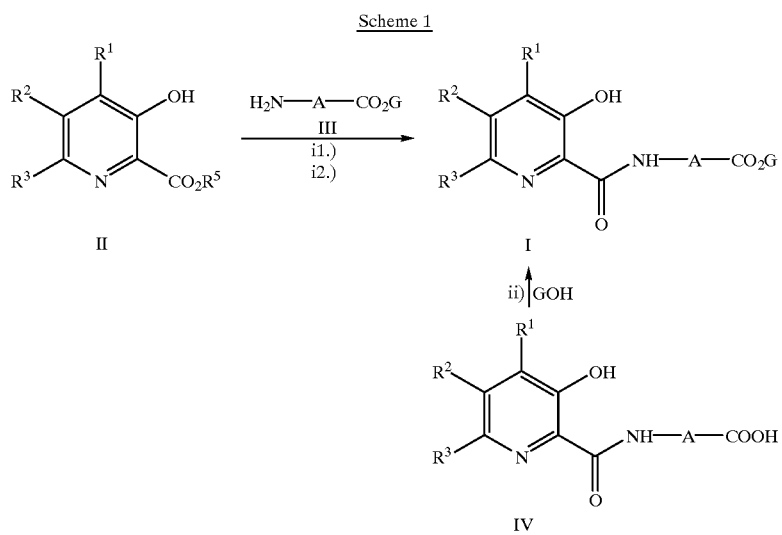

Suitable processes for amide formation (reaction i1) are the methods of carbonyl activation and the condensation reactions known from peptide chemistry. Reagents used for carboxylic acid activation can be the substances known to the person skilled in the art, such as thionyl chloride, oxalyl chloride, pivaloyl chloride, chloroformic acid ester derivatives or N,N'-carbonyldiimidazole. The activated derivatives of the compounds of the formula II are reacted in situ with the amide derivatives of the formula III after preparation.

A suitable condensing agent is, for example, the combination of N,N'-dicyclohexylcarbodiimide/N-hydroxy-1 H-benzotriazole and N-ethylmorpholine.

Suitable solvents are dichloromethane, tetrachloromethane, butyl acetate, ethyl acetate, toluene, tetrahydrofuran, dimethoxyethane, 1,4-dioxane, acetonitrile, N,N-dimethylformamide, N,N-dimethylacetamide, dimethyl sulfoxide, nitromethane and/or pyridine.

The compounds of the formula I according to the invention have valuable pharmacological properties and exhibit, in particular, antifibrotic activity.

The antifibrotic action can be determined in the following animal models: formation of a connective-tissue capsule around a subcutaneously implanted osmotic minipump, in: Unemori, E. N. et al., *J. Invest. Dermatol.*, (1993), 101:280–5, collagen content of subcutaneously implanted "cotton pellets" or polyvinyl sponges, in: Boyle, E., Mangan, F. R., *Br. J. Ep. Pathol.* (1980), 61: 351–60; and collagen content of the lung after radiation-induced or chemically induced fibrosis, in: Ward, H. E. et al., *Radiat. Res.* (1993), 136:15–21, and also Santana, A. et al. *Am. J Respir. Cell. Mol. Biol.* (1995), 13: 34–44.

Inhibition of prolyl4-hydroxylase in cell cultures: normal human dermal fibroblasts (NHDF), rat liver epithelial cells (Ref. 1) and fat storing cells from the liver (Ref. 2) are used as a cell model for substance testing. To do this, the cells are cultured in the presence of inhibitors. Simultaneously, the collagen synthesized de novo this time is metabolically labeled by 4-$^3$H-L-proline and $^{14}$C-proline. The effect of the test substances on the degree of hydroxylation of the collagen is then determined according to the method of Chojkier et al (Ref. 3). The reference substance employed is 2,2'-dipyridyl. (Ref. 1—Schrode, W., Mecke, D., Gebhard, R. (1990), "Induction of glutamine synthetase in periportal hepatocytes by co-cultivation with a liver epithelial cell line", *Eur. J. Cell. Biol.* 53: 35–41, Ref 2—Blomhoff, R., Berg T. (1990), "Isolation and cultivation of rat liver stellate cells", *Methods Enzymol.* 190: 59–71, and Ref. 3—Chojkier, M. Peterkofsky, B. Bateman, J. (1980), "A new method for determining the extent of proline hydroxylation by measuring changes in the ration of [4-$^3$H]:[$^{14}$C] proline in collagenase digests", *Anal. Biochem.* 108: 385–393).

Inhibition of prolyl-4-hydroxylase in vitro (in chicken embryo calvaria) according to Biochem. J. (1994) 300: 525–530.

1. Metabolic Labeling

Calvaria are dissected from 15-day-old chicken embryos and washed for 3 min at 37° C. in Hanks' balanced salt solution minimum essential medium Eagle (HMEM, BioWhittaker, Walkersville, Md, USA). Four calvaria each are incubated at 37° C. for 2.5 h in glass vessels with 1.5 ml of HMEM with addition of 2 mM glutamine and 1 μCi or [U-$^{14}$C] proline and various inhibitor concentrations. The incubation is ended by inserting the sample vessel in ice. The medium is removed and the calvaria are briefly washed with 1 ml of double-distilled $H_2O$. The calvaria are then treated with 3 ml of 0.5 M acetic acid and 18 pg of phenylmethanesulfonyl fluoride and extracted for 16 h. The extraction solution is dialyzed against 0.5 M acetic acid at 4° C. to remove the free [U-$^{14}$C]proline and then freeze-dried in aliquots.

2. Hydroxyproline Analysis

An aliquot of the freeze-dried sample is dissolved in 2 ml of 6 N HCl and hydrolyzed at 105° C. for 24 h. The hydrochloric acid is then evaporated. The residue is suspended in 300 μl of double-distilled $H_2O$, transferred to Eppendorf vessels and dried again. The residual hydrochlorides are neutralized by dissolving in 60 μl of an ethanol/$H_2O$/triethylamine 2:2:1 (v:v:v) and repeated drying. The amino acids are then derivatized for 20 min at room temperature in a solution of ethanol/triethylamine/phenyl isothiocyanate/H₂O 7:1:1:1 (v:v:v:v) and dried again. For analysis using HPLC, the samples are dissolved in 150 μl of a phosphate buffer (5 mM $Na_2HPO_4$, pH 7.4/acetonitrile 95:5 (v:v)) and centrifuged at 10000 g for 5 min. 50 μl are used for analysis. The HPLC chromatography is carried out on a C18 reverse phase column Ultrasphere ODS 3 μm, 4.6 mm×7.5 cm (Beckman) at 50° C. using the following gradient system:

| Time | Buffer A | Buffer B |
|---|---|---|
| 0 min | 100% | 0% |
| 0–9 min | 100–90% | 0–10% |
| 9–11 min | 90–0% | 10–100% |
| 11–12 min | 0% | 100% |
| 12–14 min | 0–100% | 100–0% |
| 14–19 min | 100% | 0% |

Soln. A: 70 mM Na acetate pH 6.14/0.1% acetonitrile
Soln. B: Acetonitrile/methanol/water 45:15:40 (v:v:v)
3. SDS Polyacrylamide Gel Electrophoresis An aliquot of the freeze-dried samples from procedure 1 is dissolved for the SDS polyacrylamide gel electrophoresis using 10 mM tris/HCl, pH 8/1 mM EDTA/1% SDS and 5% mercaptoethanol and denatured at 95° C. for 5 min. The electrophoresis carried out on a linear gradient gel (5–15%). After fixing in methanol/glacial acetic acid/water 3:1:6 (v:v:v), the gels are dried and used for the exposure of Kodak X-Omat film at –70° C.

In the following, the surprising advantages of the compounds according to the invention compared with compounds from EP-A-0 661 269 are illustrated with the aid of comparison experiments by means of the inhibition of prolyl-4-hydroxylase (collagen biosynthesis) in rat liver cells:

TABLE 1

| Example No. of EP-A-0 661 269 | Cells | Inhibition of collagen biosynthesis |
|---|---|---|
| 1 | Rat liver fat storing (Ito) cells | –50%: 53 μM |
| 1 | Rat liver epithelial cells | –50%: 38 μM |

TABLE 2

| Example No. of present application | Cells | Inhibition of collagen biosynthesis |
|---|---|---|
| 1 | Rat liver epithelial cells | –100%: 25 μM |
| 1 | Normal human dermal fibroblasts | –50%: 0.6 μM |
| 2 | Normal human dermal fibroblasts | –50%: 1.6 μM |

TABLE 3

| Example No. of present application | Tissue | Inhibition of collagen biosynthesis |
|---|---|---|
| 19 | Calavaria | –50%: <0.8 μM |
| 20 (Disclaimer) | Calavaria | –50%: <0.8 μM |

The compounds of the formula I can be used as medicaments in the form of pharmaceutical preparations which contain them, optionally with tolerable pharmaceutical vehicles. The compounds can be used as therapeutics, e.g. in the form of pharmaceutical preparations, which contain these compounds as a mixture with a pharmaceutical, organic or inorganic excipient suitable for enteral, percutaneous parenteral administration, or administration by inhalation, such as, for example water, gum arabic, gelatin, lactose, starch, magnesium stearate, talc, vegetable oils, polyalkylene glycols, petroleum jelly etc.

For this purpose, they can be administered orally in doses from 0.1 to 25 mg/kg/day, preferably 1 to 5 mg/kg/day, or parenterally in doses of 0.01 to 5 mg/kg/day, preferably 0.01 to 2.5 mg/kg/day, in particular 0.5 to 1.0 mg/kg/day. In severe cases, the dose can also be increased. In many cases, however, lower doses are sufficient. These details relate to an adult approximately 75 kg in weight.

Under the examples described below, the compounds of the formula I according to the invention are designated as substituted 3-hydroxypyridine-2-carboxylic acid ((glycyl) ester)amides. This manner of notation is understood as meaning substituted 3-hydroxypyridine-2-carboxylic acid N-((alkoxycarbonyl)methyl)amides. Classification as substituted N-(3-hydroxypyridyl-2-carbonyl)glycine esters is a further possibility.

EXAMPLE 1

3-Hydroxypyridine-2-carboxylic acid N-(((1-dodecyloxy)carbonyl)methyl)amide a) Glycine 1-dodecyl ester tosylate 38 g (0.5 mol) of glycine, 93.2 g (0.5 mol) of 1-dodecanol and 115 g (0.6 mol) of p-toluenesulfonic acid were heated in a water separator with 400 ml of toluene until water no longer passed over. 4 h after cooling, the mixture was made to crystallize by trituration, diluted with diethyl ether, and the precipitated product was filtered off with suction, washed with diethyl ether and dried. 140 g of product were obtained, m.p. 106° C. (sintering at 80° C.).

b) 7 g (50 mmol) of 3-hydroxypyridine-2-carboxylic acid were suspended in 800 ml of anhydrous dichloromethane and treated with 7.5 g (55 mmol) of 1-hydroxy-1H-benzotriazole, 19.2 ml (150 mmol) of N-ethylmorpholine, 21.2 g (50 mmol) of N-cyclohexyl-N'-(2-morpholinoethyl) carbodiimide methyl-p-toluenesulfonate (CMC) and 20.8 g (50 mmol) of glycine 1-dodecyl ester tosylate and the mixture was stirred at 20° C. for 50 h.

The precipitated urea was then filtered off with suction, the mother layer was shaken successively with 2N aqueous hydrochloric acid, with saturated, aqueous sodium bicarbonate solution and with water, the organic phase was dried and concentrated in vacuo, and the residue was chromatographed on silica gel using ethyl acetate. 12 g of pale brown oil which crystallized on standing were obtained from appropriate fractions. The mixture was treated with cold petroleum ether, the product was filtered off with suction and washed with cold petroleum ether and 8.5 g of colorless crystalline product were obtained, m.p. 53–56° C.

EXAMPLE 2

3-Hydroxypyridine-2-carboxylic acid N-(((1-butyloxy)carbonyl)methyl)amide a) Glycine 1-butyl ester tosylate 38 g (0.5 mol) of glycine were treated with 37 g (0.5 mol) of 1-butanol and 115 g (0.6 mol) of p-toluenesulfonic acid in 400 ml of toluene and the mixture was heated in a water separator until water no longer passed over. After standing overnight, the precipitated product was filtered off with suction and washed with diethyl ether; 20 g of product, m.p. 80–82° C. A further 130 g of product were obtained from the mother liquor.

b) The title compound was obtained by reacting 4.9 g (35 mmol) of 3-hydroxypyridine-4-carboxylic acid with 4.7 g (35 mmol) of 1-hydroxy-1H-benzotriazole, 19.8 ml (150 mmol) of N-ethylmorpholine, 14.8 g (35 mmol) of CMC and 10.6 g of glycine 1-butyl ester tosylate analogously to Example 1b). After chromatography of the crude product using ethyl acetate on silica gel, 3 g of oily, pale brown product were obtained.

$^1$H-NMR (DMSO, 300 MHz): δ=12.21 (s, OH), 9.45 (t, NH), 8.20 (m, 1H), 7.55 (m, 1H), 7.43 (m, 1H), 4.12 (d, CH$_2$), 4.08 (OCH$_2$), 1.56 (m, 2H), 1.33 (m, 2H), 0.88 (t, CH$_3$).

Examples 3–20 represent compounds made/can be made by a similar process.

EXAMPLE 3

3-Hydroxypyridine-2-carboxylic acid N-(((1-octyloxy)carbonyl)methyl)amide

EXAMPLE 4

3-Hydroxypyridine-2-carboxylic acid N-(((1-pentyloxy)carbonyl)methyl)amide

EXAMPLE 5

3-Hydroxypyridine-2-carboxylic acid N-(((1-hexyloxy)carbonyl)methyl)amide

EXAMPLE 6

3-Hydroxypyridine-2-carboxylic acid N-(((1-heptyloxy)carbonyl)methyl)amide

EXAMPLE 7

3-Hydroxypyridine-2-carboxylic acid N-(((1-nonyloxy)carbonyl)methyl)amide

EXAMPLE 8

3-Hydroxypyridine-2-carboxylic acid N-(((1-decyloxy)carbonyl)methyl)amide

EXAMPLE 9

3-Hydroxypyridine-2-carboxylic acid N-(((1-tetradecyloxy)carbonyl)methyl)amide

EXAMPLE 10

3-Hydroxypyridine-2-carboxylic acid N-(((1-octadecyloxy)carbonyl)methyl)amide

EXAMPLE 11

3-Hydroxypyridine-2-carboxylic acid N-[(((2-ethyl)-1-butyloxy)carbonyl)-methyl)]amide Oily substance; MS: m/e=281.3 (M$^+$+H)

EXAMPLE 12

3-Hydroxypyridine-2-carboxylic acid N-(((1-tridecyloxy)carbonyl)methyl)amide

EXAMPLE 13

3-Hydroxypyridine-2-carboxylic acid N-(((1-hexadecyloxy)carbonyl)methyl)amide

EXAMPLE 14

3-Hydroxypyridine-2-carboxylic acid N-(((1-(cis-9-octadecenyl)oxy)carbonyl)-methyl)amide

EXAMPLE 15

3-Hydroxypyridine-2-carboxylic acid N-(((1-(trans-3-hexenyl)oxy)carbonyl)-methyl)amide

EXAMPLE 16

3-Hydroxypyridine-2-carboxylic acid N-(((1-(3-methylbutyl)oxy)carbonyl)-methyl)amide

EXAMPLE 17

3-Hydroxypyridine-2-carboxylic acid N-(((1-propyloxy)carbonyl)methyl)amide

EXAMPLE 18

3-Hydroxypyridine-2-carboxylic acid N-(((2-propyloxy)carbonyl)methyl)amide

EXAMPLE 19

3-Hydroxypyridine-2-carboxylic acid N-(((3-pentyloxy)carbonyl)methyl)amide, m.p. 84° C. (from n-heptane/ethyl acetate (5:1))

EXAMPLE 20

3-Hydroxypyridine-2-carboxylic acid ((glycyl) ethyl ester)amide (J. Org. Chem. 31, 636–638 (1966)).

What is claimed is:

1. A compound of the formula I wherein
$R^1$, $R^2$ and $R^3$ are hydrogen,
A is a —CH$_2$— group, in which a hydrogen atom can be replaced by a methyl group, and
B is —CO$_2$G, wherein
G is a branched or unbranched (C$_1$–C$_{20}$)-alkyl radical, a branched or unbranched (C$_2$–C$_{20}$)-alkenyl radical, a branched or unbranched (C$_2$–C$_{20}$)-alkynyl radical, a branched or unbranched (C$_4$–C$_{20}$)-alkenynyl radical, or a (C$_3$–C$_{12}$)-cyloalkyl radical, or a physiologically active salt of said compound,
and excluding 3-hydroxypyridine-2-carboxylic acid ((glycyl) ethyl ester)amide.

2. A compound of the formula I as claimed in claim 1, wherein $R^1$, $R^2$ and $R^3$ are hydrogen, A is a —$CH_2$— group, in which a hydrogen atom can be replaced by a methyl group, and B is —$CO_2G$, wherein G is a branched or unbranched ($C_1$–$C_{20}$)-alkyl radical, a branched or unbranched ($C_2$–$C_{20}$,)-alkenyl radical, a branched or unbranched ($C_2$–$C_{20}$)-alkynyl radical, a branched or unbranched ($C_4$–$C_{20}$)-alkenynyl radical, or a ($C_3$–$C_{12}$)-cycloalkyl radical, wherein the above radicals contain one or more substituents selected from hydroxyl, halogen, cyano, trifluoromethyl, carboxyl, ($C_1$–$C_{12}$)-alkyl, ($C_3$–$C_8$)-cycloalkyl, ($C_5$–$C_8$)-cycloalkenyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_1$–$C_8$)-hydroxyalkyl, ($C_1$–$C_{12}$)-alkylcarbonyloxy, and ($C_3$–$C_8$)-cycloalkyl-carbonyloxy;

or a physiologically active salt of said compound,
and excluding 3-hydroxypyridine-2-carboxylic acid ((glycyl) ethyl ester)amide.

3. A compound of the formula I as claimed in claim 1, wherein $R^1$, $R^2$ and $R^3$ are hydrogen, A is a —$CH_2$— group in which a hydrogen atom can be replaced by a methyl group, and B is —$CO_2G$, wherein G is a branched or unbranched aliphatic ($C_1$–$C_{18}$)-alkyl radical, a ($C_3$–$C_8$)-cycloalkyl radical, a ($C_3$–$C_8$)-cycloalkyl-($C_1$–$C_8$)-alkyl radical, a branched or unbranched ($C_2$–$C_{18}$)-alkenyl radical, wherein the above radicals contain one or more substituents selected from hydroxyl, ($C_1$–$C_4$)-alkoxy, ($C_1$–$C_6$)-alkylcarbonyloxy, and ($C_3$–$C_8$)-cycloalkylcarbonyloxy, or a physiologically active salt of said compound,
and excluding 3-hydroxypyridine-2-carboxylic acid ((glycyl) ethyl ester)amide.

4. A compound of the formula I as claimed in claim 1, wherein $R^1$, $R^2$ and $R_3$ are hydrogen, A is a —$CH_2$— group in which a hydrogen atom can be replaced by a methyl group, and B is —$CO_2G$, wherein G is a branched or unbranched aliphatic ($C_1$–$C_{18}$)-alkyl radical, a ($C_3$–$C_4$)-cycloalkyl radical, a ($C_3$–$C_8$)-cycloalkyl-($C_1$–$C_8$)-alkyl radical, a branched or unbranched ($C_2$–$C_{18}$)-alkenyl radical selected from a geranyl, a farnesyl, and a branched or unbranched ($C_2$–$C_{18}$)-alkynyl radical, wherein the above radicals contain a substituent selected from hydroxyl, ($C_1$–$C_4$)-alkoxy, ($C_1$–$C_6$)-alkylcarbonyloxy, and ($C_3$–$C_8$)-cycloalkyl-carbonyloxy, or a physiologically active salt of said compound,
and excluding 3-hydroxypyridine-2-carboxylic acid ((glycyl) ethyl ester)amide.

5. A compound of the formula I as claimed in claim 1, wherein $R^1$, $R^2$ and $R^3$ are hydrogen, A is a —$CH_2$— group, in which a hydrogen atom can be replaced by a methyl group, and B is —$CO_2G$, wherein G is a branched or unbranched aliphatic ($C_1$–$C_{18}$)-alkyl radical, a ($C_5$–$C_6$)-cycloalkyl radical, a ($C_3$–$C_8$)-cycloalkyl-($C_1$–$C_4$)-alkyl radical, or a branched or unbranched ($C_2$–$C_{18}$)-alkenyl radical, or a physiologically active salt of said compound,
and excluding 3-hydroxypyridine-2-carboxylic acid ((glycyl) ethyl ester)amide.

6. A compound of the formula I as claimed in claim 1, wherein $R^1$, $R^2$ and $R^3$ are hydrogen, A is a —$CH_2$— group, in which a hydrogen atom can be replaced by a methyl group, and B is —$CO_2G$, wherein G is a branched or unbranched ($C_1$–$C_{18}$)-alkyl or a ($C_2$–$C_{18}$)-alkenyl radical, or a physiologically active salt of said compound,
and excluding 3-hydroxypyridine-2-carboxylic acid ((glycyl) ethyl ester)amide.

7. A compound of the formula I as claimed in claim 1, wherein $R^1$, $R^2$ and $R^3$ are hydrogen, A is a —$CH_2$— group, and B is —$CO_2G$, wherein G is a branched or unbranched ($C_1$–$C_{18}$)-alkyl or a ($C_2$–$C_{18}$)-alkenyl radical, or a physiologically active salt of said compound,
and excluding 3-hydroxypyridine-2-carboxylic acid ((glycyl) ethyl ester)amide.

8. A compound of the formula I as claimed in claim 1, wherein $R^1$, $R^2$ and $R^3$ are hydrogen, A is a —$CH_2$— group, B is —$CO_2G$, wherein G is a linear ($C_1$–$C_{18}$)-alkyl radical, or a physiologically active salt of said compound,
and excluding 3-hydroxypyridine-2-carboxylic acid ((glycyl) ethyl ester)amide.

9. A process for the preparation of a compound of the formula I as claimed in claim 1, wherein A is a —$CH_2$— group in which a hydrogen atom can be replaced by a methyl group, and B is $CO_2G$, which comprises i1.) reacting a pyridine-2-carboxylic acid of the formula II ($R^5$=H) with an amino ester of the formula III or a salt thereof to give an amidoester of the formula I; or i2.) reacting a pyridine-2-carboxylic acid ester of the formula II ($R^5$=lower alkyl=($C_1$–$C_5$)-alkyl) under a condition of aminolysis to give a compound of the formula I

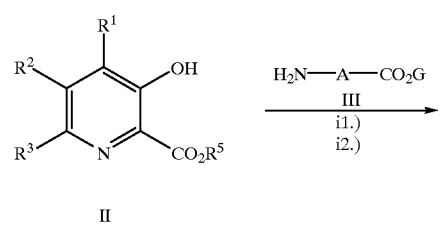

II

-continued

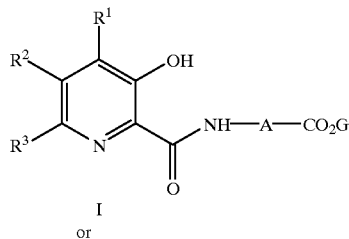

or

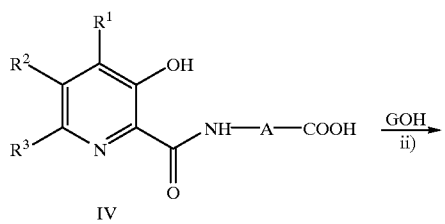

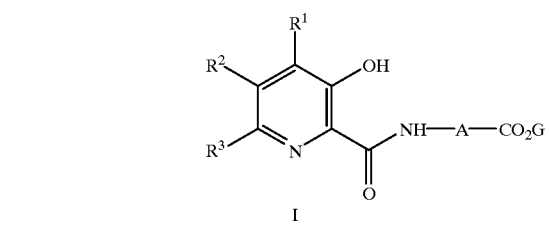

10. A method for the inhibition of prolyl-4-hydroxylase in vivo which comprises administering to a host in need of such treatment an effective amount of a compound of the formula I

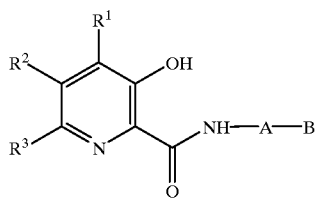

wherein

R$^1$, R$^2$ and R$^3$ are hydrogen,

A is a —CH$_2$— group, in which a hydrogen atom can be replaced by a methyl group, and B is —CO$_2$G, wherein G is a branched or unbranched (C$_1$–C$_{20}$)-alkyl radical, a branched or unbranched (C$_2$–C$_{20}$)-alkenyl radical, a branched or unbranched (C$_2$–C$_{20}$)-alkynyl radical, a branched or unbranched (C$_4$–C$_{20}$)-alkenynyl radical, or a (C$_3$–C$_{12}$)-cycloalkyl radical, or a physiologically active salt of said compound.

11. A method for the inhibition of collagen biosynthesis which comprises administering to a host in need of such treatment an effective amount of a compound of the formula I

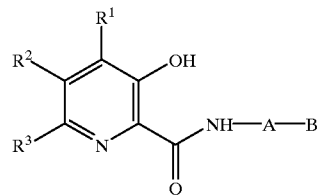

wherein

R$^1$, R$^2$ and R$^3$ are hydrogen,

A is a —CH$_2$— group, in which a hydrogen atom can be replaced by a methyl group, and B is —CO$_2$G, wherein G is a branched or unbranched (C$_1$–C$_{20}$)-alkyl radical, a branched or unbranched (C$_2$–C$_{20}$)-alkenyl radical, a branched or unbranched (C$_2$–C$_{20}$)-alkynyl radical, a branched or unbranched (C$_4$–C$_{20}$)-alkenynyl radical, or a (C$_3$–C$_{12}$)-cycloalkyl radical, or a physiologically active salt of said compound.

12. A method for the avoidance and/or reduction of a deposit of connective tissue in a diseased human organ which comprises administering to a host in need of such treatment an effective amount of a compound of the formula I

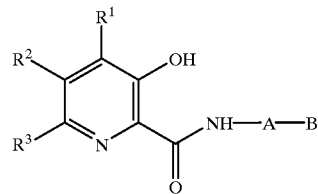

wherein

R$^1$, R$^2$ and R$^3$ are hydrogen,

A is a —CH$_2$— group, in which a hydrogen atom can be replaced by a methyl group, and B is —CO$_2$G, wherein G is a branched or unbranched (C$_1$–C$_{20}$)-alkyl radical, a branched or unbranched (C$_2$–C$_{20}$)-alkanyl radical, a branched or unbranched (C$_2$–C$_{20}$)-alkenyl radical, a branched or unbranched (C$_4$–C$_{20}$)-alkenynyl radical, or a (C$_3$–C$_{12}$)-cycloalkyl radical, or a physiologically active salt of said compound.

13. A method for the treatment of a fibrotic disorder which comprises administering to a host in need of such treatment an effective amount of a compound of the formula I

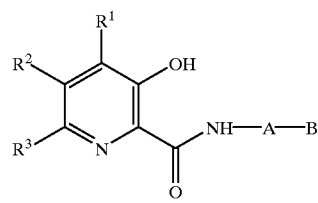

wherein

R$^1$, R$^2$ and R$^3$ are hydrogen,

A is a —CH$_2$— group, in which a hydrogen atom can be replaced by a methyl group, and B is —CO$_2$G, wherein G is a branched or unbranched (C$_1$–C$_{20}$)-alkyl radical, a branched or unbranched (C$_2$–C$_{20}$)-alkenyl radical, a branched or unbranched (C$_2$–C$_{20}$)-alkynyl radical, a branched or unbranched (C$_4$–C$_{20}$) alkenynyl radical, or a (C$_3$–C$_{12}$)-cycloalkyl radical, or a physiologically active salt of said compound.

14. A method for the treatment of a fibrotic disorder as claimed in claim 13 wherein the fibrotic disorder is of the lung, the liver, the kidney, the heart, the eye, or the skin or in atherosclerosis.

15. A method for the treatment of a fibrotic disorder as claimed in claim 13 wherein the treatment takes place locally and/or systemically.

16. A method for the treatment of a fibrotic disorder as claimed in claim 15 wherein the local treatment is for an avoidance and/or reduction of a scar after a surgical intervention of the human body.

17. A method as claimed in claim 10 for local treatment in a case of increased formation of connective tissue in skin.

18. A method as claimed in claim 10 for local treatment in a case of increased formation of connective tissue in a lung.

19. A method as claimed in claim 10 for local treatment in a case of increased formation of connective tissue in an eye.

20. A pharmaceutical composition comprising an effective amount of a compound the formula I

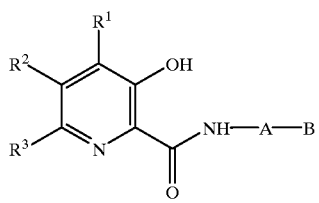

(I)

wherein

R$^1$, R$^2$ and R$^3$ are hydrogen,

A is a —CH$_2$— group, in which a hydrogen atom can be replaced by a methyl group, and B is —CO$_2$G, wherein G is a branched or unbranched (C$_1$–C$_{20}$)-alkyl radical, a branched or unbranched (C$_2$–C$_{20}$)-alkenyl radical, a branched or unbranched (C$_2$–C$_{20}$)-alkynyl radical, a branched or unbranched (C$_4$–C$_{20}$)-alkenynyl radical, or a (C$_3$–C$_{12}$)-cycloalkyl radical, or a physiologically active salt of said compound and together with a pharmaceutically suitable or physiologically tolerable excipient, additive and/or auxiliary.

21. A method for the inhibition of prolyl-4-hydroxylase in vivo which comprises administering a pharmaceutical composition as claimed in claim 20.

22. A method for the inhibition of collagen biosynthesis which comprises administering a pharmaceutical composition as claimed in claim 20.

23. A method for the avoidance and/or reduction of a deposit of connective tissue in a diseased human organ which comprises administering a pharmaceutical composition as claimed in claim 20.

24. A method for the treatment of a fibrotic disorder which comprises administering a pharmaceutical composition as claimed in claim 20.

25. A method for the treatment of a fibrotic disorder as claimed in claim 24 wherein the fibrotic disorder is of the lung, the liver, the kidney, the heart, the eye, or the skin or in atherosclerosis.

26. A method for the treatment of a fibrotic disorder as claimed in claim 24 wherein the treatment takes place locally and/or systemically.

27. A method for the treatment of a fibrotic disorder as claimed in claim 26 wherein the local treatment is for an avoidance and/or reduction of a scar after a surgical intervention of the human body.

28. A method as claimed in claim 21 for local treatment in a case of increased formation of connective tissue in skin.

29. A method as claimed in claim 21 for local treatment in a case of increased formation of connective tissue in a lung.

30. A method as claimed in claim 21 for local treatment in a case of increased formation of connective tissue in an eye.

* * * * *

UNITED STATES PATENT AND TRADEMARK OFFICE
CERTIFICATE OF CORRECTION

PATENT NO. : 6,020,350
DATED : February 1, 2000
INVENTOR(S) : Klaus Weidmann et al.

It is certified that error appears in the above-identified patent and that said Letters Patent is hereby corrected as shown below:

On the title page item [57], before line 1, insert

"3-hydroxypyridine-2-carboxamidoesters, their preparation and their use as pharmaceuticals"

On the Title Page, Item [57], in the Abstract, line 1, "hydrixypyridine" should read --hydroxypyridine--.

Claim 2, col. 11, line 12, "$(C_2-C_{20},)$-alkenyl" should read --$(C_2-C_{20})$-alkenyl--.

Claim 4, col. 11, line 46, "$R_3$" should read --$R^3$--.

Claim 4, col. 11, line 51, "$(C_3-C_4)$-cycloalkyl" should read --$(C_3-C_8)$-cycloalkyl--.

Claim 9, col. 13, line 10, after "or", insert the line --ii) esterifying a compound of the formula IV with an alcohol GOH.--.

Claim 12, col. 14, line 47, "$(C_2-C_{20})$-alkanyl" should read --$(C_2-C_{20})$-alkenyl--.

Claim 12, col. 14, line 48, "$(C_2-C_{20})$-alkenyl" should read --$(C_2-C_{20})$-alkynyl--.

Claim 20, col. 15, line 30, after "compound", insert --of--.

UNITED STATES PATENT AND TRADEMARK OFFICE
CERTIFICATE OF CORRECTION

PATENT NO. : 6,020,350
DATED : February 1, 2000
INVENTOR(S) : Klaus Weidmann et al.

It is certified that error appears in the above-identified patent and that said Letters Patent is hereby corrected as shown below:

Claim 20, col. 16, line 4, before "branched", insert --a--.

Signed and Sealed this

Thirtieth Day of January, 2001

Attest:

Q. TODD DICKINSON

Attesting Officer

Director of Patents and Trademarks